United States Patent
Altshuler

[11] Patent Number: 6,036,635
[45] Date of Patent: Mar. 14, 2000

[54] ERECTION CONTROL SYSTEM

[76] Inventor: Yakov Altshuler, 66 Overlook Ter. #2E, New York, N.Y. 10040

[21] Appl. No.: 08/805,498

[22] Filed: Feb. 26, 1997

[51] Int. Cl.⁷ ...................................................... A61F 5/41
[52] U.S. Cl. ............................................................. 600/38
[58] Field of Search .......................................... 600/38–41

[56] References Cited

U.S. PATENT DOCUMENTS

| | | | |
|---|---|---|---|
| 3,744,486 | 7/1973 | Wilson . | |
| 3,820,533 | 6/1974 | Jones . | |
| 4,175,554 | 11/1979 | Gerow . | |
| 4,203,432 | 5/1980 | Koch . | |
| 4,378,008 | 3/1983 | Osbon, Sr. . | |
| 4,539,980 | 9/1985 | Chaney . | |
| 4,628,915 | 12/1986 | Chaney . | |
| 4,641,638 | 2/1987 | Perry . | |
| 4,690,135 | 9/1987 | Gerow . | |
| 4,718,411 | 1/1988 | Stewart . | |
| 4,741,329 | 5/1988 | Marcune . | |
| 4,753,227 | 6/1988 | Yanuck, Jr. . | |
| 4,856,498 | 8/1989 | Osbon . | |
| 4,856,499 | 8/1989 | Kelly . | |
| 4,960,113 | 10/1990 | Seeberg-Elverfeldt . | |
| 4,995,381 | 2/1991 | Marmar et al. . | |
| 5,020,552 | 6/1991 | Stewart . | |
| 5,095,895 | 3/1992 | Walsh . | |
| 5,115,800 | 5/1992 | Matejevic et al. . | |
| 5,125,890 | 6/1992 | Merill et al. | 600/39 |
| 5,195,943 | 3/1993 | Chaney | 600/41 |
| 5,213,563 | 5/1993 | Cox | 600/38 |
| 5,221,251 | 6/1993 | Edminster | 600/41 |
| 5,234,402 | 8/1993 | Osbon | 600/41 |
| 5,243,968 | 9/1993 | Byun | 600/38 |
| 5,244,453 | 9/1993 | Osbon et al. . | |
| 5,306,227 | 4/1994 | Osbon | 600/41 |
| 5,338,288 | 8/1994 | Finkle | 600/41 |
| 5,344,389 | 9/1994 | Walsdorf et al. | 600/41 |
| 5,421,324 | 6/1995 | Kelly | 600/39 |
| 5,421,808 | 6/1995 | Osbon et al. | 600/38 |
| 5,707,341 | 1/1998 | Mathewuse | 600/39 |

FOREIGN PATENT DOCUMENTS 347300  8/1960  Switzerland ............................. 600/39

OTHER PUBLICATIONS

Urology, pp. 126–131, Feb. 1986, Nadig et al., Noninvasive Device To Produce and Maintain an Erection–like State.

Urologic Clinics of North America v. 15, pp. 123–128, Feb. 1988, Witherington, Suction Device Therapy in the Management of Erectile Impotence.

British Medical Journal v.296, pp. 161–162, Jan. 1988, Wiles, Successful non–invasive management of erectile impotence in diabetic men.

(List continued on next page.)

Primary Examiner—Samuel Gilbert

[57] ABSTRACT

Erection control system of the invention overcomes known deficiencies of vacuum constriction devices, especially cumbersomness, technical difficulties and painfulness.

A penis-shaped vacuum chamber (12) adapted for unnoticeable operation under user's cloth. Removably placed penile seal (14) and a baffle (16) are adjustable to the user's penile girth and provide attachment so that the vacuum chamber hangs on the user's penis without additional support.

A ribbon-shaped constriction device (26) is wound with multiple turns over each other to form a cylindrical ring, retained by the belt (28) for exerting a prearranged inward radial pressure. A transferring device with the pulling loop (40) dislodges constriction device together with removably placed penile seal and baffle onto erect penis with simultaneous release of vacuum without additional mechanisms. The removably placed penile seal, the baffle, the belt are formed from segments of a condom. A method of vacuum erection treatment with a vacuum chamber, removable seal, a vacuum source and constriction device, in which forcible slip off of the constriction device onto erected penis causes slip off of the removable seal with simultaneous vacuum release in the vacuum chamber has been proposed.

12 Claims, 2 Drawing Sheets

OTHER PUBLICATIONS

Journ. of Urology v. 140.pp. 975–979, Nov. 1988, Marmar et al., The Use of a Vacuum Constriction Device To Augment a Partial Erection.

Jorn. of Urology v. 141, pp. 320–322, 1989, Witherington, Vaccum Constriction Device for Management of Erectile Impotence.

Journ. of Urology v. 142, pp. 1087–1089, 1989, Diederichs et al., The Effect of Subatmospheric Pressure on the Simian Penis.

Journ. of Urology v. 142,p. 1086, 1989, Sharlip, Vacuum–Induced Erection.

Journ. of Urology v. 144,pp. 79–82, 1990, Turner et al., Vacuum Devices To Treat Erectile Disfunction.

Diabetic Medicine v.8, pp. 964–967, 1991, Price et al., The Management of Impotence in Diabetic Men by Vacuum Tumescence Therapy.

Journ. of Urology v. 149, pp. 1285–1287, May 1993, Meinhardt et al., The Negative Pressure Device for Erectile Disorders: When Does It Fail?.

Brit. Journ. of Ur., 1994, Vrijhof et al., Vacuum constriction devices in erectile disfunction: acceptance and effectiveness in patients with impotence of organic and mixed aetiology.

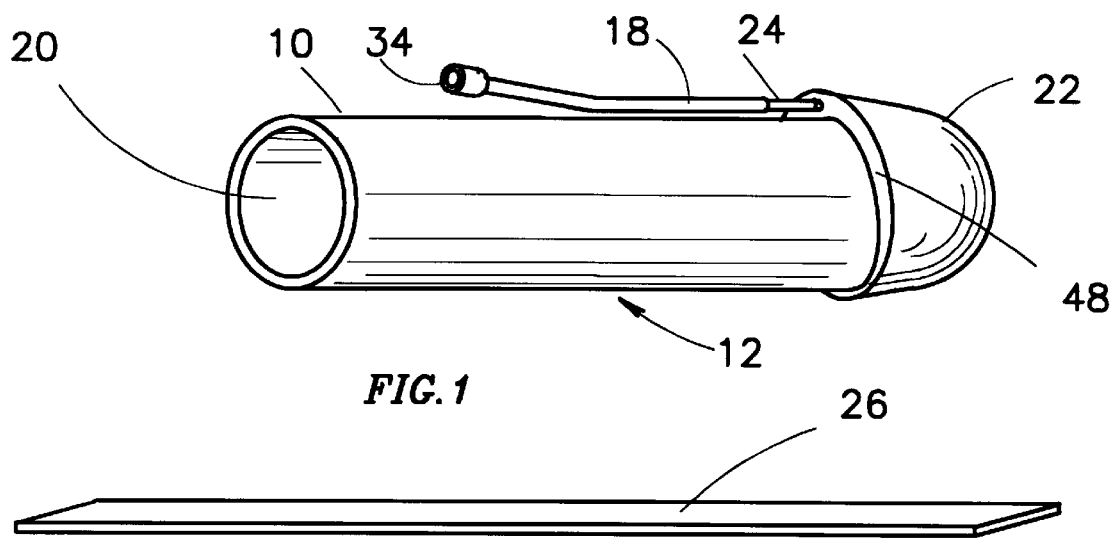
FIG.1
FIG.2
FIG.3
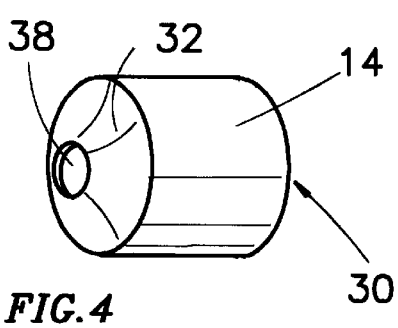
FIG.4
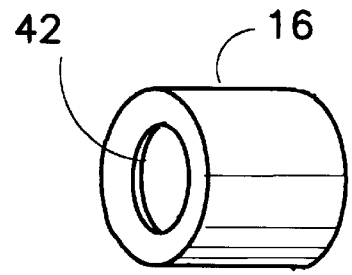
FIG.5
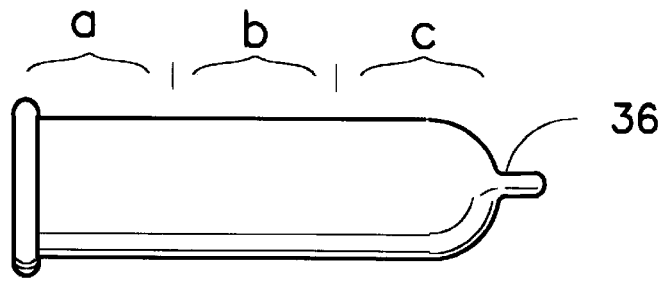
FIG.6

ERECTION CONTROL SYSTEM

BACKGROUND

1. Field of Invention

The invention relates to vacuum constriction devices and therapy for erectile dysfunction treatment and augmenting male potency.

2. Description of Prior Art.

The acceptance of a vacuum constriction therapy has dramatically changed during the last decade. Considered as a doubtful 10–12 years ago, nowadays it is recognized as the first line remedy, preferable to other treatments of erection dysfunction—sex therapy, self injections, venous and arterial surgery, implantation of a penile prosthesis. With the vacuum constriction device sex function can be returned to its original state, bypassing many psychological problems. Numerous studies and surveys show that vacuum constriction therapy can help patients to improve sexual satisfaction, decrease psychiatric symptomatology, increase self-esteem. (Roy Witherington, "Suction Device Therapy in the Management of Erectile Impotence", Urologic Clinics of North America v. 15, No. 1, February 1988); D. E. Price et al. "The Management of Impotence in Diabetic Men by Vacuum Tumescence Therapy", Diabetic Medicine, 1991; 964–967). W. Meinhardt et al. "The Negative Pressure Device for Erectile Disorders: When Does It Fail?"; Journal of Urology, v. 149, p.p. 1285–87, May 1993.)

Presently manufactured vacuum constriction devices comprise a vacuum chamber with an open end serving as an entrance, a closed end connected to a vacuum pump through a hose, and constriction rings placed on the vacuum chamber close to its open end. To achieve an erection the penis is inserted into the open end of the vacuum chamber which is pressed to abdomen to provide an airtight seal. Then the vacuum is generated in the chamber with the manually or electrically operated vacuum pump. The partial vacuum inside the chamber causes the blood flow into the penis thus producing erection. To sustain the erection the constriction ring preliminary installed on the vacuum chamber is forced to slip off onto the root of the penis. Being placed on the root of the penis the constriction ring inhibits the blood flow from the penis thus sustaining erection. After this the vacuum is released, the chamber is removed from the erect penis.

In addition to listed major components, a vacuum constriction device may have auxiliary components or assemblies to facilitate constrictor's placement onto the vacuum chamber and dislodging them, appliance for equalizing pressure inside and outside the vacuum chamber after dislodging of constrictor, vacuum gauge etc.

Besides benefits listed above, existing vacuum constriction devices have substantial drawbacks and deficiencies which make them unacceptable to many users.

The most often drawbacks and reasons for rejection of known vacuum constriction devices are: pain, technical difficulties, inhibition of sexual behavior, painful placing of constriction rings and painful removal, insufficient erection, pivoting, blocking of ejaculation. (H. J. E. J. Vrijhof and K. P. J. Delaere "Vacuum Constriction Devices in Erectile Dysfunction: Acceptance and Effectiveness in Patients With Impotence of Organic or Mixed Aetiology", British Journal of Urology, 1994, 74, 102–105; S. Althof et al. "Through the Eyes of Women: The Sexual and Psychological Responses of Women to Their Partner's Treatment With Self-Injection or External Vacuum Therapy", The Journal of Urology, v. 147, 1024–1027, April 1992; Louisa A. Turner and associates "Treating Erectile Dysfunction With External Vacuum Devices: Impact Upon Sexual, Psychological and Marital Functioning", The Journal of Urology, v. 144; 79–82; 1990.

To make vacuum constriction therapy acceptable to users at large, substantial changes and improvements have to be introduced into comercially available devices.

Major inconveniences and deficiencies of prior art devices stem from their design features, methods of airtight sealing, constriction, method of simultaneous release of vacuum. Problems of design and function pertinent to prior art are discussed below.

Abdominal seal

In commercially available vacuum constriction devices the airtight seal is provided by pressing the open end of the chamber against the abdomen. In this case the scrotal tissue is encircled by vacuum chamber from very beginning and as soon as the negative pressure is applied the scrotal tissue is pulled into the chamber. It could be painful and even dangerous especially if the testicle is drawn in.

Penile airtight seal around the penis substantially reduces chances of suction of the scrotal tissue and testicle into the chamber. An air tight seal removably attached to the vacuum chamber is disclosed in Swiss Patent of Jun. 30, 1960 to G. Meldi. An elastic membrane with peripheral border which is folded over the vacuum chamber has a short sleeve in the center defining the orifice which corresponds to that of a flaccid penis so that it is not squeezed when being introduced into the chamber. There are significant drawbacks in such air tight seal:

a) as there must be a clearance between the orifice and the flaccid penis, the device has to be pressed against the abdomen, i.e. the seal is abdominal. Only after creation of vacuum and engorgement of the penis the sleeve functions as a penile seal, b) the membrane cannot be used with vacuum chambers which do not have protruding lips or flanges for folding membrane's peripheral borders over them. Such lips and flanges would hinder the transfer of constrictors from vacuum chamber, c) because of its complex shape, fabrication of Meldi's membrane require expensive molding equipment which greatly increases device's cost, d) in Meldi's device the diameter of the orifice has to be larger and correspond to that of the flaccid penis to prevent squeezing during its introduction into the chamber. According to the Kinsey Institute of Sex Research penile diameters are in a range from 1.2 to 5.4 cm. To provide membranes with sleeves' diameters corresponding this range of penile diameters will require a plurality of molds which will make production prohibitively expensive.

Meldi's device does not have a separate constriction device. The same sleeve of Meldi's membrane functions as a constrictor. The deficiencies of this approach will be discussed further.

Vacuum devices with airtight seals around the penis capable to accommodate wider range of penile girths are disclosed in U.S. Pat. No. 5,125,890, Jun. 30, 1992 to D. Merill et. al.; U.S. Pat. No. 5,243,968, Sep. 14, 1993 to Kyoung Byun. Diaphragms described in these patents are permanently attached to the vacuum chamber with special provisions to prevent their detachment.

In a Merill et al. patent, (reference numerals in parenthesis) the sealing diaphragm (7) is formed from elastic tubing approximately 7.5 cm long, 2.5 cm in diameter and 0.1 cm wall thickness. The tubing is stretched over the outside wall of the chamber so that it firmly grips the chamber's wall. The grip of the stretched tubing actually has to be stronger than the grip of at least two constriction rings placed over it, so that during dislodging of constrictors the diaphragm will not slip off.

These are the conditions determining that according to specification the wall thickness of the tubing has to be at least about 0.1 cm. Because of substantial force needed to extend the diaphragm, a special skills and tooling are required. The user cannot reinstall or replace the diaphragm in case of a damage or slip off.

While providing benefits of a penile seal diaphragm mentioned above, a diaphragm disclosed in Merill's patent has substantial drawbacks associated with the requirements of a firm grip to prevent slip off from the vacuum chamber.

Dislodging with simultaneous vacuum release facilitates quick and easy removal of the vacuum chamber from erect penis. Vacuum release must be simultaneous with dislodging. The tumescence disappears immediately with releasing of vacuum unless the base of the penis is constricted. (W. Diderichs et al. "The effect of subatmospheric pressure on the simian penis", The Journal of Urology, 142, 1087–1089, 1989).

Known in prior art solution provide valves or holes which become automatically open during dislodging of constricting device.

R. Yanuck (U.S. Pat. No. 4,753,227, Jun. 28, 1988) provides mechanism which actuates a spring loaded arm with the sealing plug. The construction involves a plurality of small precise parts, fabrication and assembling of which increase device's cost. The mechanism enlarges the diameter of the vacuum chamber which complicates placement of the constriction device. Solutions without valves are disclosed in U.S. Pat. No. 5,244,453, Sep. 14, 1993 to Osbon and U.S. Pat. No. 5,338,288, Aug. 16, 1994 to E. Finkle. Osbon discloses a plurality of vent holes connecting interior of the vacuum chamber with the atmosphere. Holes formed in a groove perpendicular to the chamber's axis are covered by the constriction ring. Dislodging of the constriction ring opens the vent holes and releases vacuum in the chamber. It is difficult to keep all holes perfectly sealed by the constriction ring. Besides, the groove hinders constriction ring's movement off the chamber, the ring has to be extended to overcome groove's edge which may result in premature release of the vacuum.

In Finkle's patent only one vent hole is provided. This hole is covered by one of a turns of a multiturn constrictor band wound around the chamber. Again, as soon as this turn shifts, vacuum may be released prematurely.

Merill's (supra) patent also provides a function of simultaneous dislodging of constriction device and automatic releasing of vacuum.

The vacuum chamber and penile seal diaphragm have air holes (38), (40), a constriction band dislodging strap (36) has a plug (42), attached under its surface so that it enters and seals air holes. The constriction band (8) is positioned over the strap (36) with attached plug (42) to hold the plug firmly in air holes (38), (40). An upward pull of the strap draws plug from air holes and relieves the vacuum in the chamber while simultaneously dislodging constriction band (8). The air holes, the plug and the placement of the constricting band has to be precisely aligned which is difficult. The slightest displacement or deformation of diaphragm's air holes or plug or position of the constriction band will disturb air tightness with deterioration of vacuum.

Constriction device

No other part or component influences more on efficacy of a vacuum erection system than constriction device. Recognition of this problem is reflected in numerous surveys, reports and patents for improvements of constriction devices.

Prior art constriction devices may be subdivided into three major functional groups:

1. placed directly on erect penis;
2. placed on flaccid penis with inducing erection after placement;
3. preliminary placed on vacuum chamber and forced to slip off on a root of erect penis.

Constriction devices of group 1 are disclosed in U.S. patents as: U.S. Pat. Nos. 5,421,324; 5,370,601; 5,327,910; 5,246,015; 5,221,251; 5,085,209; 4,967,738; 4,834,115; 4,203,432; 3,773,040; 3,759,253; 2,581,114 and others. There is no provision in devices' designs for the use with vacuum chambers. Because of the limited use of constriction devices of this group we do not review them in detail.

Constriction devices of group 2 are unitary members combining function of a seal and a constriction device. These devices may be subdivided into three subgroups, depending on how the constriction is produced.

Subgroup 2a

In Meldi's device (Swiss patent No. 347 300, supra) diameter of constrictor's aperture is larger than diameter of flaccid penis. The constriction occures when engorging penis presses aperture from inside. With given diameter of the sleeve the only way to increase radial pressure is to augment engorgement by increasing degree of vacuum, which can be dangerously excessive. Penile engorgement is limited by individual user's anatomy. With existing range of penile diameters from 1.2 to 5.4 cm (Kinsey Institute of Sex Research, supra) a substantial number of membranes with different diameters has to be provided to select one which fits the individual user's anatomy.

In subgroup 2b a constrictor has a collar with aperture smaller then cross section of a flaccid penis. It is placed on the flaccid penis after which a vacuum erection device is applied and activated to achieve erection. The constrictor has a skirt large enough to cover the entrance of the vacuum tube and to provide airtight seal. The penis is pulled through the aperture so that the device is placed on a penile root, a vacuum chamber is applied and constriction is produced by penile engorgement. Examples of this subgroup are disclosed in U.S. Pat. No. 5,344,389, "Combination Seal and Constriction Device", Walsdorf et al. Sep. 6, 1994; U.S. Pat. No. 5,234,402, "Apparatus and Method for Augmenting Male Potency With User Tissue Protection", James B. Osbon, Aug. 10, 1993.

The device of Walsdorf et al. comprises a cylindrical collar with radially extending skirt, concentrical to the collar. The device is applied to the user's penis with the aid of the applicator assembly. A plurality of devices with different diameters of collars has to be provided to select one to accommodate erect penile size of a particular user. External vacuum erection chamber has to be held and pressed against the skirt all time during operation to avoid deterioration of vacuum.

The device of James B. Osbon (U.S. Pat. No. 5,234,402) has analogous deficiencies.

Constriction devices of subgroup 2c use inflatable ring encircling the penis. Inflatable constriction devices working with vacuum chambers are disclosed in U.S. Pat. Nos. 4,641,638, "Sexual Erection Prosthesis and Method of Use", Robert D. Perry, Feb. 10, 1987; 3,820,533 "Surgical Device with Suction Means", Jones, Aug. 2, 1971;

Inflatable constriction devices have an advantage in providing smooth control of pressure exerted on erect penis and rapid release of constriction when needed. To direct pressure inward they must have a hard shell, which limits contacting part of the penis and can hurt female partner during penetration.

Devices of group 3 are disclosed in U.S. patents: U.S. Pat. Nos. 5,338,288 "Noninvasive Male Potency Device", Eugene Finkle, Aug. 16, 1994; 5,195,943, "Male Organ Restrictor Ring Applicator", John Chaney, Mar. 23, 1993; 5,125,890 "Vacuum-Constriction Erection Aid Device", D. S. Merill et al. Jun. 30, 1992 (supra); 5,115,800, "Apparatus for Achieving and Maintaining Penis Erection", Matejevic et al.; 5,095,895, May 26, 1992, "Negative Pressure Erection Apparatus", Michael Walsh, Mar. 17, 1992; 5,083,556, "Penile Cincture Band Operational Apparatus", Osbon et al., Jan. 28, 1992; 4,856,498, "Vacuum Generating and Constriction Apparatus", Osbon et al., Aug. 15, 1989; 4,856,499, "Erection Device", Edward C. Kelly, Aug. 15, 1989; 4,753,227, "Erection Device and Method", Rudolph R. Yanuck, Jun. 28, 1988; 4,741,329, "Surgical Appliance for Stimulating an Erection", Benjamin F. Marcune, May 3, 1988 4,539,980 "Male Organ Conditioner", John L. Chaney, Sep. 10, 1985; 4,378,008, "Erection Aid Device", Gedding Osbon, Mar. 29, 1983; 3,744,486 "Apparatus for Obtaining an Artificial Erection" Eldon M. Wilson, Jul. 10, 1973.

Constrictors used in known vacuum constriction devices generally comprise a ring of elastic rubber with C-shaped handles for removal from the erect penis. Detailed descriptions of constriction rings are disclosed in U.S. Pat. No. 5,306,227, "Apparatus for Augmenting Male Potency", to Robert and James Osbon on Apr. 26, 1994 and U.S. Pat. No. 4,539,980, "Male Organ Conditioner", to John L. Chaney on Sep. 10, 1985 (supra). To provide sufficient inward pressure on erect penis, one or more of constriction rings have to be placed at the edge of an open end of the vacuum chamber. Placing the ring on the edge of the vacuum chamber requires strong fingers and dexterity, many of users do not have. Recognizing this problem, special cone-shaped applicator have been proposed. (U.S. Pat. No. 5,083,556, "Penile Cincture Band Operational Apparatus", to Osbon et al. on Jan. 28, 1992; U.S. Pat. No. 5,020,522 "Compact Vacuum Therapy System", to Edward T. Stuart on Jun. 4, 1991; U.S. Pat. No. 4,539,980 (supra); "Male Organ Conditioner Accessory", to John. L. Chaney on Dec. 16, 1986).

Accessories and apparatus facilitate the problem, but complicate the device and increase its cost. Device for transfering of a constriction ring is disclosed in U.S. Pat. No. 5,195,943 "Male Organ Restrictor Ring Applicator", to John L. Chaney on Mar. 23, 1993 uses moving and fixed cam elements on the vacuum chamber.

Disclosed in U.S. Pat. No. 5,115,800 "Apparatus For Achieving and Maintaining Penis Erection" to Matejevic et al. on May 26, 1992 (supra) uses mechanism of lever and belt, making vacuum erection device mechanically complicated and substantially increasing dimensions and cost.

Complains on pain are often caused by imperfection of constriction rings. Rings are molded of natural or synthetic rubber with different durometer number. To provide acceptable inward pressure, selection for individual users is based on size, durometer and a number of constriction rings used together. Despite high cost due to a number of expensive molds, there is no way to provide smooth control of the pressure which happens to be excessive and causes discomfort, numbness, bruises.

Discomfort and pain can also be caused by twisting of doubled rings during their transfer onto the penis and because of intertwining with pubic hair. Removal of constriction ring from erect penis could be painful, especially when two or more rings are used together; after removal of the first ring the penis is still engorged, as the remaining ring prevents blood outflow.

Known are in prior art linear elastomeric constrictors wound around vacuum chamber.

U.S. Pat. No. 3,744,486 "Apparatus for Obtaining an Artificial Erection", to Eldon M. Wilson on Jul. 10, 1973 (supra) discloses an elastic restrictor mounted tightly upon the exterior surface of the entrance tube. There is no teaching in the disclosed text about the key features of the multiturn constrictor, particularly, how the constrictor is kept in a tightened condition after wrapping around the chamber and how it is released from erect penis.

U.S. Pat. No. 5,338,288, "Noninvasive Male Potency Device" to Eugene Finkle on Aug. 16, 1994 (supra) discloses a constrictor device, which is a length of elastomeric material with knots near each end. The constrictor is initially wound around a vacuum cylinder with a plurality of turns, and the distal knotted end is tucked underneath the proximal knotted end. For removal, the constrictor has to be pulled on eather end.

This approach has advantage in increased safety against excessed pressure as the device allows a gradual pressure variations. But there are also serious drawbacks: during transfer from the vacuum cylinder turns are twisting and pinch skin and pubic hair. But the strongest pain is during unwrapping of the constrictor and return to its original unstretched size. Individual turns of constrictor abruptly change their cross section and length with pinching of penile skin and producing painful sawing action.

Pivoting is another deficiency inherent to all known vacuum constriction devices. In prior art constriction rings the inward radial pressure is applied to a narrow annular surface of the penis. Retaining the blood in the sponge bodies, constriction rings keep the penis engorged. The sponge bodies between the penile root and the ring are filled much less because of blood outflow. This causes pivoting—an engorged penis behaves as attached by hinges, which eventually presents the mayor difference between natural erection and one maintained with the use of constriction device.

SUMMARY OF THE INVENTION

Erection control system of the invention overcomes known deficiencies of vacuum constriction devices, especially cumbersomness, technical difficulties and painfulness.

The system is made up of devices, components and parts: vacuum chamber removably placed penile seal, baffle, constriction device with controllable inward pressure, transferring device, manual or electrical vacuum pump, which can be used for building erection control systems of different complexity.

Removably placed penile seal and a baffle allow customization of the vacuum chamber to individual users anatomy. Due to the wide range of accommodated penile girth, customization is reduced to selection of chamber's length slightly longer than the user's penis.

A penis-shaped vacuum chamber is adapted for unnoticeable operation under user's cloth. The use of the device can be concealed.

Removably placed penile seal and a baffle provide attachment so that the vacuum chamber hangs on the user's penis without additional support and prevents suction of the scrotal tissue.

The invention provides constriction device with controllable inward radial pressure.

A ribbon-shaped constriction device is wound with multyple turns over each other to form a cylindrical ring with the length of generatrix equal to the width of the ribbon. The constriction device is retained by the belt also serving for releasing of constriction device for removal after activity.

A transfering device with the pulling loop dislodges constriction device together with removably placed penile seal (and the baffle, if used in the system) onto erect penis with simultaneous release of vacuum without additional mechanisms.

The removably placed penile seal, the baffle, the belt are formed from segments of a condom.

A method of vacuum erection treatment with a vacuum chamber, removable seal means, a vacuum source and constriction device, in which forcible slip off of the constriction device onto erect penis causes slip off of the removable seal means with simultaneous vacuum release in the vacuum chamber.

BRIEF DESCRIPTION OF THE DRAWINGS

FIG. 1 is a general view of vacuum chamber;

FIG. 2 is a view of a constriction ribbon;

FIG. 2a is a view of a constriction ribbon with urethral relief;

FIG. 3 is view of a removably placed penile seal;

FIG. 4 is a view of a baffle;

FIG. 5 shows the use of a condom for forming a removably placed penile seal, a baffle and a belt;

FIG. 6 illustrates a transfering device with a pulling loop and retaining tube;

Figure 7:
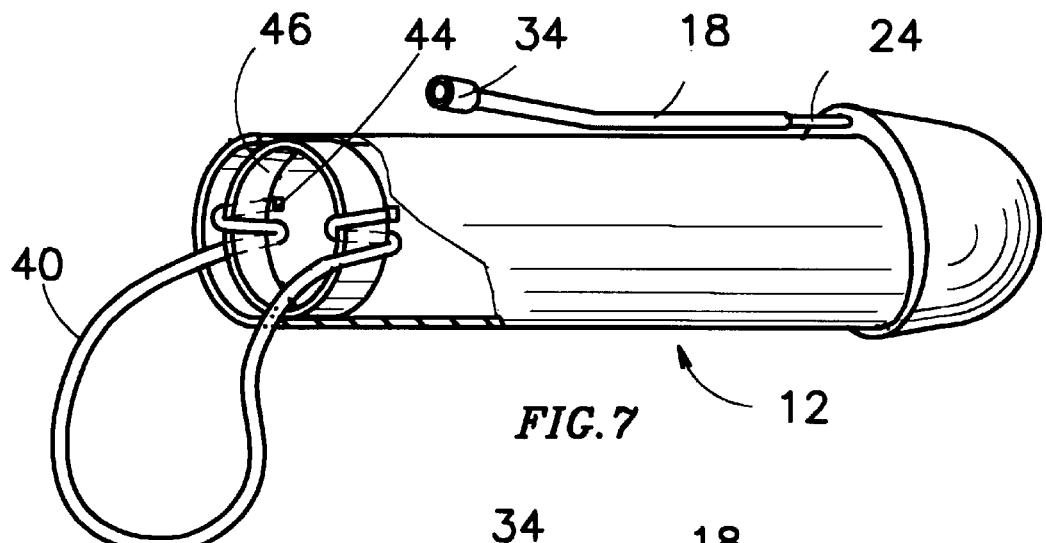
FIG. 7 is a view of the vacuum chamber with transferring device, seal, baffle.

REFERENCE NUMERALS IN DRAWINGS 10 cylinder
12 vacuum chamber
14 removably placed penile seal
16 baffle for adjustment to penile girth
18 hose
20 entrance
22 dome
24 fitting
26 constriction ribbon
28 belt
30 cylinder-shaped portion of penile seal
32 cone-shaped portion of penile seal
34 luer
36 condom's reservoir's tip
38 seal's orifice
40 pulling loop
42 baffle's aperture
44 knotted end of the pulling loop
46 retaining tube
48 ridge
50 urethral relief channel Erection Control System with Removably Placed Penile Seal

DESCRIPTION OF PREFERRED EMBODIMENT

Erection control system is made up of vacuum chamber, vacuum source, removably placed penile seal, constriction device. Vacuum chamber 12 (FIG. 1), made of transparent plastic material, has a cylinder 10 with an open end serving as an entrance 20. At the distal end the vacuum chamber is closed by dome 22 with a fitting 24 for connecting chamber 12 to the vacuum source. A ridge 48 is protecting fitting 24 and giving the vacuum chamber penis-like shape. A vacuum chamber may be composed of two parts: cylinder 10 and dome 22 cemented together. The length of the vacuum chamber varies from 12 to 24 cm to fit individual user's anatomy. Fitting 24 is made of a hypodermic stainless steel with outside diameter about 0.2 cm, the wall thickness about 0.02 cm and about 2.5 cm long. A short hose 18 with luer 34 is attached to fitting 24 for convenient connection to the vacuum source through the mating luer.

Erection control system with removably placed penile seal can work with known commercially available vacuum chambers. The vacuum chamber of the present invention is preferable due to special advantages:

(a) It overcomes cumbersomness. It does not have outward projecting mechanical parts like levers, pumps, heavy hoses. It is compact and portable.

(b) Customizing of the vacuum chamber according to individual user's anatomy is eventually reduced to selecting the length of its cylindrical part 10, as adjustment to penile girth is provided by cutting the orifice of the penile seal, performed by the user as explained further.

(c) The use of the device is easy to conceal. It facilitates operation under the user's cloth, as proposed penile seal allows the chamber to hang on the penis wirhout support under partial vacuum.

Due to the domed penis-like shape of the chamber it does not hinder upward movement during growing erection. Besides, certain deformation of the cloth produces an impression of an erect penis but not of a frightening mechanical tool inside, which eliminates known reasons for embarrassment or inferiority feelings.

Figure 8:
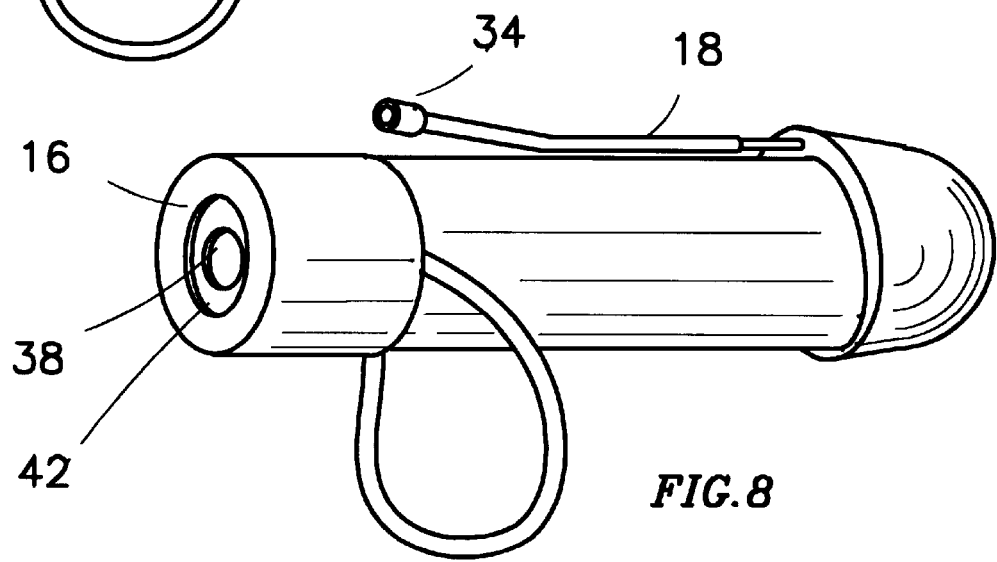
FIG. 8 is a view of the vacuum chamber with removably placed penile seal, baffle, constriction ring and a belt.
Figure 9:
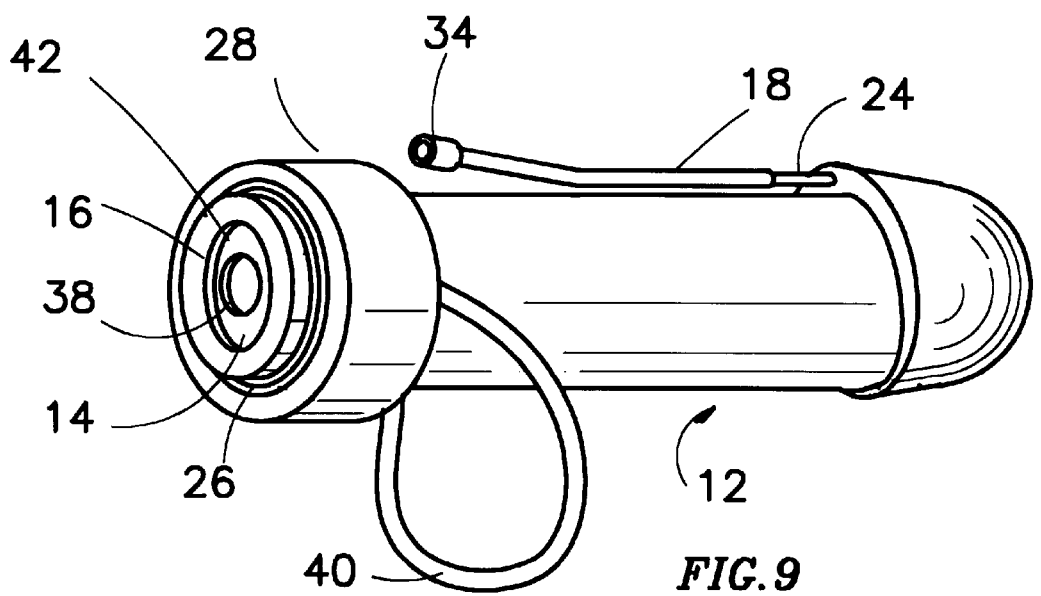

Removably placed penile seal 14, shown on FIGS. 3, 7, 8 is an elastic member with the wall thickness in a range from about 0.005 cm to about 0.01 cm having a cylindrical portion 30 and a cone-shape portion 32. The cylindrical portion having larger diameter slidably fits the outside surface of the vacuum chamber at the proximal end. It is suitable for easy slip off during transfer. A cone-shaped portion covers the entrance of the vacuum chamber. Its orifice 38 forms a penile seal and provides air tightness between the penis and the chamber.

The concept of the removably placed penile seal is quite opposite to the concept of Merill's (supra) penile seal diaphragm: instead of firm grip for preventing slip off of the vacuum chamber during removal of constricting device, the removably placed penile seal of the invention is adapted to easily slip off from the vacuum chamber during transfer. This allows to fabricate removably placed penile seal from an extra thin tubing, many times (for example, 20 times) thinner than in above mentioned patent. Instead of a tube with the wall thickness of at least 0.1 cm (Merill), removably placed penile seal according to the invention may have wall thickness of 0.005 cm, which provides advantages described further.

The disposable airtight penile seal can be made of a segment "c" of a condom by cutting the tip of the condom's reservoir. The tip of the condom 36, is cut, for example, by scissors thus forming orifice 38 of the seal (FIGS. 3, 7). The further from the tip is the cut, the wider is orifice 38 of the seal. This enables the user to optimize the seal according to penile girth. The orifice has to be smaller than the diameter of the user's flaccid glans penis.

The removably placed penile seal has a number of important advantages:
1. it eliminates the need in a special vacuum releasing mechanism as the vacuum is released simultaneously with removal of penile seal from the vacuum chamber;
2. it enables adjustment to different penile girths and facilitates customizing to user's anatomy;
3. it does not require special skill and tooling for placement on a vacuum chamber. The removably placed penile seal made of a condom has additional advantages:
4. it fully conforms to the requirements for medical devices contacting the human skin;
5. it does not hurt glans penis during removal of erect penis from the vacuum chamber;
6. it allows easy installation of a second adjaced seal to improve tightness;
7. it is always available and inexpensive.

Operation of the Embodiment

A personal lubricant such as sold under the mark K-Y (Advanced Care Products, Ortho Pharmaceutical Corp., Raritan, N.J.) is applied to the outside surface of the proximal end of the chamber to about 1 cm from the edge.

Penile seal 14 is removably placed on the proximal end of the vacuum chamber 12.

The system can work with commercially available constriction rings. The ring is placed over the removably placed penile seal as shown on FIG. 8.

When glans penis touches the orifice 38 of removably placed penile seal 14, it closes the orifice and enables creating of vacuum in the chamber. The penis is sucked into the chamber, engorges and becomes erect.

To sustain erection, constriction device has to be transferred onto the erect penis. Removably placed penile seal is adapted to be easily slipped off from the vacuum chamber during transfer. Lubrication of the vacuum chamber's surface facilitates slip off. The constriction device in this embodiment is forced to slip off from the vacuum chamber by pushing with fingers (not shown).

With the throwing of penile seal 14 the chamber opens with simultaneous release of vacuum. This is an importabnt advantage of removably placed penile seal of the invention: dislodging of separate constriction device with simultaneos releasing of vacuum without any special additional mechanism. By contrast to the device with abdominal seal which has to be pressed against the abdomen, the vacuum chamber with penile seal can be pulled in the opposite direction during vacuum generation, which facilitates better engorgement of the glans penis. Another important advantage of removably placed penile seal is enabling the system to be in a "stand-by" mode. To operate a prior art erection constriction device the user have to stay undressed, to hold the device and the pump with both hands. It is inconvenient, but without hand support an occasional disturbing of airtight abdominal seal could cause detachment, fall and damage of the device. With the system built according to present invention this does not happen: after introduction of the penis into the vacuum chamber it is sucked in and held by the orifice of the removable penile seal. The grip increases with penile tumescence, but even with releasing of vacuum inside the chamber the penis detumescens slowly because of certain constriction effect produced by penile seal. This is a "stand-by" mode from which full erection can be achieved in the shortest time. Being connected to vacuum pump kept in the user's pocket, the erection control system may be operated unnoticeably at user's convenience. Dome-shaped distal end of the vacuum chamber facilitates under cloth operation: cloth does not hinder vacuum chamber's move to erect position.

Erection Control System with Removably Placed Penile Seal and a Baffle

DESCRIPTION OF PREFERRED EMBODIMENT

FIG. 4 shows a cup-shaped baffle 16 with an aperture 42 which facilitates air tight seal, hinders sucking in of a scrotal tissue and helps to keep the vacuum chamber hanging on the penis without support. Baffle 16 covers penile seal placed on the proximal end of the vacuum chamber. Aperture 38 is slightly smaller than the girth of the erect penis. An adjustment to the required size is provided by pulling the baffle walls along the chamber. Pulling the walls toward the closed end of the chamber extends the aperture 42 and makes it larger. When used with the baffle, orifice 38 is approximately concentric to baffle aperture 42. The baffle can be sormed from the entrance section of the condom ("a", FIG. 5)

The baffle has several functions and advantages:
1. it enables adjustment to different penile girths and facilitates customizing to the user's anatomy,
2. it prevents pulling scrotal tissue into the chamber during vacuum generation;
3. it facilitates wearing the erection control system in a "stand-by" position and producing full erection at the proper moment without delay;
4. it works as additional constrictor in a vacuum constriction system.

Erection Control System with Removably Placed Penile Seal, a Baffle, and a Transferring Device

DESCRIPTION OF PREFERRED EMBODIMENT

FIG. 6 shows a transferring device according to present invention. The device consists of retaining tube 46 and pulling loop 40. The retaining tube 46 made of transparent plastics is about 4 cm long, the wall thickness is about 0.15 cm. The retaining tube 46 slidably fits to the inside surface of the vacuum chamber 12 so that its proximal edge is completely inside the chamber at about 2 cm from the chamber's proximal edge. The retaining tube 46, inserted into the proximal segment of the vacuum chamber, squeezes end segments of the pulling loop, pressing them to the inside wall of the vacuum chamber The pulling loop 40 is made of a textile strip or an extra strong cotton covered polyester (like Dual Duty Plus, manufactured by Clark Co.) with the length of a doubled thread about 20 cm. The knots 44 at the ends of the loop are positioned beyond the distal edge of the retaining tube 46 to prevent pulling them out during transfer. The angular distance between segments of pulling loop as they exit the vacuum chamber 12 is adjustable during assembling (reinstallation). The preferable angle for easier transfering of the constricting device is about 120 degree.

Operation of the Embodiment

Prior to placement of the constricting device, the hanging part of the pulling loop shown at FIG. 6 is placed over the outside surface of the vacuum chamber and stretched towards its distal end. Then the removably placed penile seal, the baffle, and the constriction device are placed over the proximal end of the vacuum chamber. All parts assembled on a vacuum tube connected to the vacuum pump are shown on FIG. 8. By pulling the loop 40 towards the open end, the constricting device is easily transferred onto erect penis. In this case the pulling loop simultaneously dislodges the removably placed penile seal 14, the baffle 16 and the constriction device 26 with the instant vacuum release in the chamber.

The Constriction Device with Controllable Inward Pressure

DESCRIPTION OF PREFERRED EMBODIMENT

FIG. 8 shows a constriction device mounted on a cylindrical surface of the vacuum chamber 12. The constricting ribbon 26 is wound around the cylindrical surface and is covered by the belt 28 to form a constriction device with a prearranged inward radial pressure. FIG. 2 shows the constriction ribbon 26 as it looks before being wound. The constriction ribbon is made of elastic and soft material, for example, of silicon rubber or latex with generally rectangular cross section. Approximate dimension of the flat ribbon: width—about 2 cm, thickness about 0.1–0.3 cm, length about 30 cm.

FIG. 2*a* shows the ribbon with a channel 50 for urethral relief which has a cross section of a semicircle with diameter about 0.3 cm in a bulged segment of the constricting ribbon. A bulged segment has gradually increasing and diminishing thickness; the thickness of the bulged segment at channel 50 is about 0.6 cm, the segment's length is about 6 cm.

A belt 28, shown on FIG. 8, comprises an elastic tubular element with diameter about 3–4 cm, wall thickness from about 0.005 to 0.05 cm and about 3 cm long. The belt provides several major functions: (a)—it serves as a shell encircling constricting ribbon wound with multiple turns, keeping the constrictor with a prearranged inward pressure; (b)—it serves for unlocking of constrictor, for which purpose the belt 28 is pulled upward allowing easy release of the constricting ribbon 26. (c)—it adds certain constricting force to the device.

Preferred embodiment of belt 28 comprises a segment of a condom ("b", FIG. 5).

Operation of the Embodiment

Constriction ribbon 26 is wound with the tension by multiple turns over the segment of the proximal end of cylindrical surface of the vacuum chamber. During the first turn an end of the constrictor is pressed by the user's thumb to the tube. At the second turn the constricting ribbon is wound over the first turn then over the second and so on. After being wound with desired number of turns, which is usually from 3 to 5, the end of the constricting ribbon is pressed by the user's thumb to the vacuum chamber 12. Then the belt 28 is pulled over the wound constricting ribbon 26.

Operation of multiturn wrapping of the constrictor with urethral relief is the same as described above.

During transfering of the constriction device the channel 50 covers the urethra, providing protection from excessive constriction and allowing free discharge of the seminal fluid.

To transfer constriction device the user applies his finger to the loop 40 and pulls it towards perineum. There is a great number of possibilities of providing proper pressure of the constricting device: by selection of constricting ribbon's material, cross section, length, number of turns in different combinations. With constrictor and belt of given properties and dimensions, the user may prearrange desirable pressure by changing the number of turns during wrapping. The present invention radically reduces major technical difficulties of constriction ring accociated with its placement on the vacuum chamber. A multyturn constriction ribbon is much easier to apply than a solid constriction ring. The force necessary to extend multyturn constrictor is about in a number of turns lesser than in the case of a conventional constrictor ring. A belt 28 may be easily extended during covering of the tighten constriction ribbon. At the same time, the invention eliminates the major drawback of prior art multyturn constrictors: a pain caused by individual turns on user's skin during placement and removing of constrictor. In the present invention the penile skin is protected from painful sawing action during unwrapping and releasing of the constrictor. The ribbon is wide, each next turn covers the previous, the sawing action is excluded as turns are not positioned side by side. Fabricated from medical grade materials, constriction ribbon provides strength, comfort, flexibility, improving blood circulation and eliminating harmful affects of shear and friction forces against the skin.

Although the description above contains many specificities, these should not be construed as limiting the scope of the invention but as merely providing illustrations of some of the presently preferred embodiments of this invention. Possible are further modifications, for example, a vacuum chamber may be molded as a single part, a pulling loop may be made of a thin strip instead of a reinforced thread, a retaining tube in transfering device may be placed over the vacuum chamber. Many other variations are possible with the device still remaining simple and economical.

What is claimed is:

1. An erection control system for erectile dysfunction treatment and augmenting of male potency by vacuum erection therapy:

a) a tubular vacuum chamber having a closed distal end, an open proximal end, an inside surface and an outside surface;

b) vacuum generating means connected to said vacuum chamber for producing vacuum in said vacuum chamber;

c) seal means removably placed on said proximal end of s aid vacuum chamber for forming a penile seal between said vacuum chamber and the flaccid penis;

d) a constriction device removably placed on said vacuum chamber over said seal means and adapted to drag said seal means when forced to slip off from said vacuum chamber onto erect penis, whereby simultaneous release of vacuum in said vacuum chamber occurs, wherein a portion of the seal means is positioned between the constriction device and said vacuum chamber.

2. The erection control system according to claim 1 wherein said seal means is an elastomeric resiliant member having a cylindrical portion slideably placed on said outside surface of said proximal end, and a cone-shaped portion covering said open proximal end, said cone-shaped portion having a centrally located orifice adapted to be closed by the flaccid penis, whereby an air tight penile seal between the penis and said vacuum chamber is formed.

3. The erection control system according to claim 2, wherein said seal means is formed from a segment of a condom about 5 cm long including reservoir truncated for forming an orifice adapted to provide said airtight penile seal.

4. The erection control system according to claim 1 further including a baffle means removably placed on the vacuum chamber at said open proximal end for securing attachment so that said vacuum chamber is adapted to hang on the penis without additional support and is adapted to hinder scrotal tissue from being sucked into said vacuum chamber while applying said vacuum, said baffle means comprising an elastic member having substantially a shape of a cup with an aperture in a bottom of said cup adapted for conforming to an engorging penis.

5. The erection control system according to claim 4, wherein said baffle means is formed from a segment of a condom about 5 cm long including a ring defining said aperture of said baffle means.

6. The erection control system according to claim 1, further including a transfering device with attachment means for attaching the transferring device to the vacuum chamber placed adjacent to said inside surface of said vacuum chamber, and a pulling loop having a first portion sandwiched between said attachment means and said inside surface of said vacuum chamber, a second portion placed between said seal means and said outside surface of said vacuum chamber and a third portion including a handle.

7. The erection control system according to claim 6, wherein said attachment means is a transparent retaining tube slidably inserted into the proximal segment of said vacuum chamber to sandwich said first portion of said pulling loop between said retaining tube and said inside surface of said vacuum chamber, said pulling loop is formed from a length of extra strong thread having knots at both ends adapted to prevent detachment of said loop during simultaneous transfer of said seal means and said constriction device onto erect penis.

8. An erection control system for erectile dysfunction treatment and augmenting of male potency by vacuum constriction therapy, comprising:

a) a tubular vacuum chamber having a closed distal end, an open proximal end, an inside surface and an outside surface;

b) means for connecting a vacuum source to said vacuum chamber for producing vacuum therein;

c) a constriction device of multiple turns of an elastic ribbon wound over each other to form a cylindrical ring removably mounted on said tubular vacuum chamber, said device being adapted to be transferred onto an erect penis to exert prearranged pressure thereon for hindering blood outflow therefrom, said constriction device includes constriction means for constricting and releaseable belt means for retaining said constriction means in a state with prearranged inward radial pressure, said releaseable belt means is a tubular elastic member removably placed over said constriction means;

d) a seal means on said vacuum chamber for forming a seal to retain the vacuum in said vacuum chamber when a flaccid penis is inserted thereinto and the chamber is evacuated.

9. The erection control system according to claim 8 wherein said elastic ribbon has substantially rectangular cross section with width about 2.5 cm, thickness about 0.3 cm, length about 30 cm.

10. The erection control system according to claim 9, wherein said ribbon includes an integrally and gradually elevated area about 5 cm long and about 0.5 cm high at the end of said ribbon and includes a channel means across said ribbon adapted for protecting urethra from excessive constriction and hindering of seminal fluid discharge.

11. The erection control system according to claim 8, wherein said releaseable belt means is formed from a segment of a condom with the length about 5 cm open from both sides.

12. A method of vacuum erection treatment with automatic vacuum release in a system with a vacuum chamber having a proximal end, removable penile seal including an orifice, a constriction device and a vacuum source, comprising the steps of:

a). positioning said removable penile seal over said proximal end of said vacuum chamber so that said orifice is approximately concentrical with the open end of said vacuum chamber, b). positioning said constriction device over said penile seal at said proximal end of said vacuum chamber, c). creating erection by introducing the penis through the orifice of said penile seal and applying vacuum into said vacuum chamber, and d). forcing said separate constriction device to slip off from said vacuum chamber together with said removable seal onto the erect penis, whereby vacuum in said vacuum chamber is released simultaneosly.

* * * * *